United States Patent [19]
Carlson et al.

[11] Patent Number: 5,316,908
[45] Date of Patent: May 31, 1994

[54] SIZE MARKERS FOR ELECTROPHORETIC ANALYSIS OF DNA

[75] Inventors: David P. Carlson; Paul C. Watkins; Leonard Klevan, all of Gaithersburg, Md.

[73] Assignee: Life Technologies, Inc., Gaithersburg, Md.

[21] Appl. No.: 522,406

[22] Filed: Jul. 13, 1990

[51] Int. Cl.$^5$ .............................................. C12Q 1/68
[52] U.S. Cl. ...................................... 435/6; 435/967; 436/8
[58] Field of Search ................ 435/6, 7.4, 967; 436/8; 935/1, 76, 78

[56] References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,500,707 | 2/1985 | Caruthers et al. | 536/27 |
| 4,668,777 | 5/1987 | Caruthers et al. | 536/27 |
| 4,762,779 | 8/1988 | Snitman | 436/6 |
| 4,771,384 | 9/1988 | Daniels et al. | 935/75 |
| 4,965,349 | 10/1990 | Woo et al. | 536/27 |

FOREIGN PATENT DOCUMENTS 63-113359  5/1988  Japan.
WO89/09780  10/1989  PCT Int'l Appl..

OTHER PUBLICATIONS

Pharmacia Catalogue, "Molecular Weight Markers", p. 23.
Gralla, Proc. Natl. Acad. Sci. USA, vol. 82, May 1985, Rapid "footprinting" on supercoiled DNA, pp. 3078–3081. pp. 3078–3081.
Carman et al., J. Clin. Microb., Nov. 1989, vol. 27, No. 11, Detection of Enzymatically Amplified Human Immunodeficiency Virus DNA by Oligonucleotide Solution Hybridization and by Incorporation of Radiolabeled Deoxynucleotides, pp. 2570–2573.
Budowle and Baechtel, Appl. Theor. Electrophoresis 1: 1989 GIBCO/BRL Catalogue & Reference Guide, Life Technologies, Inc., Gaithersburg, Md., pp. 3,4, 8–18, 21, 22, 24, 26, 27, 29, 30 and 32.
1989–1990 New England Biolabs, Inc. Catalog, pp. 9–11, 14–20, 23, 24, 26, 28, 29, 31 and 33.
Package inserts supplied with Ava I, Ava II, Bam H I, Bgl I, Bgl II, Bst E II, Cfo I, Cla I, Cvn I, Dde I, Dra I, Eco R I, Eco R V, Hae II, Hin c II, Hin d III, Hin f I, Msp I, Nci I, Nco I, Nde I, Nsi I, Rsa I, Sau 3A I, Sma I, Ssp I, SstI, Tha I, Xba I, and Xho I which were available on Jul. 13, 1990 and supplied by BRL/Life Technologies, Inc.
Bernards et al., Chemical Abstracts, No. 92470r, Huang J. et al., Chemical Abstracts No. 34093a 107(5):175 (1987).
Jones C. P. et al., Chemical Abstracts No. 230760h 112(25):172 (1990).
Rickwood D. et al., Practical Approaches in Biochemistry Series, pp. 227–232, Appendix I.
European Search Report for Applicants' Co-pending European Application EP O 466 404 A1.

*Primary Examiner*—Amelia Burgess Yarbrough
*Attorney, Agent, or Firm*—Sterne, Kessler, Goldstein & Fox

[57] ABSTRACT

The present invention discloses a DNA marker ladder useful in Southern blot hybridizations. The ladder is made up of pooled DNA restriction endonuclease digests, where each restriction digest contains at least one fragment complementary to a probe and at least one fragment not complementary to the probe. The regions of complementarity between the probe and the complementary fragments are double-stranded segments of the fragments. The ladder is characterized by an approximately even spacing of bands, resulting from choosing fragments having an logarithmic size distribution. Kits incorporating this ladder and a probe or means for making a probe or a probe and a means for labeling a probe are also disclosed.

32 Claims, 1 Drawing Sheet

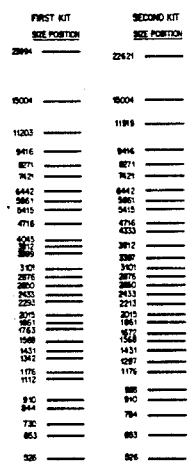

| FIRST KIT SIZE POSITION | SECOND KIT SIZE POSITION |
|---|---|
| 23994 — | 22621 — |
| 15004 — | 15004 — |
|  | 11919 — |
| 11203 — |  |
| 9416 — | 9416 — |
| 8271 — | 8271 — |
| 7421 — | 7421 — |
| 6442 — | 6442 — |
| 5861 — | 5861 — |
| 5415 — | 5415 — |
| 4716 — | 4716 — |
|  | 4333 — |
| 4045 — |  |
| 3812 — | 3812 — |
| 3599 — |  |
|  | 3397 — |
| 3101 — | 3101 — |
| 2876 — | 2876 — |
| 2650 — | 2650 — |
| 2433 — | 2433 — |
| 2293 — | 2213 — |
| 2015 — | 2015 — |
| 1861 — | 1861 — |
| 1763 — |  |
|  | 1672 — |
| 1568 — | 1568 — |
| 1431 — | 1431 — |
| 1342 — |  |
|  | 1287 — |
| 1176 — | 1176 — |
| 1112 — |  |
|  | 993 — |
| 910 — | 910 — |
| 844 — |  |
|  | 784 — |
| 730 — |  |
| 653 — | 653 — |
| 526 — | 526 — |

FIG.1

SIZE MARKERS FOR ELECTROPHORETIC ANALYSIS OF DNA

FIELD OF THE INVENTION

The present invention is in the field of molecular biology and specifically relates to the technique of gel electrophoresis of nucleic acid fragments.

BACKGROUND OF THE INVENTION

A number of mixtures of nucleic acid fragments are commercially available that can be used as markers for determining the sizes of nucleic acid molecules of experimental interest. For example, Collaborative Research, Inc. (Lexington, Mass.) has sold a marker ladder ("Quik-Kit Size Markers", cat. no. 30013) that is a mixture of 12 bacteriophage λ (lambda) fragments. They are visualized by hybridization with two $^{32}$P-labeled 12-nucleotide synthetic oligonucleotides, complementary to the left and right bacteriophage cos sites.

A large number of other DNA marker fragments are available from numerous suppliers. In every case, except the Collaborative markers, these marker fragments are restriction digests of several bacteriophage or plasmid DNAS. Every DNA fragment in the digests can then be visualized by hybridization to the same bacteriophage or plasmid DNAS.

Other DNA marker ladders often use collections of fragments that have a quasi-random size distribution. For example, the quasi-random size distribution may be made by a digest of a DNA, often λ DNA, by a single restriction enzyme. Alternatively, the fragments may vary linearly with molecular weight, i.e. adjacent bands may differ by about 1000 base pairs (e.g. "1 Kb DNA Ladder", cat. no. 5615SA, BRL, Gaithersburg, Md.). Bands in these linear ladders are not evenly spaced after electrophoresis, they are "compressed" in the "upper", higher molecular weight region of a gel. However some ladders have been constructed and sold that are logarithmically spaced ("GenePrint ™", cat. no. DG1911, Promega, Madison, Wis.).

SUMMARY OF THE INVENTION

The drawback of conventional marker ladders is that the signal generated by each fragment is proportional to its length. As a result, levels of signal that allow visualization of small fragments (e.g. 500 base pairs (bp)) give too much signal in large fragments (e.g. 20 kbp) for optimal resolution. This drawback is overcome in the marker ladder of the present invention.

The invention consists of a "target DNA" and a "probe DNA". Target DNA is constructed by pooling several restriction endonuclease digests of a single DNA of known sequence. Each restriction endonuclease digest generates a number of DNA fragments, one of which contains a specific sequence "S". The restriction endonucleases and the sequence "S" are chosen so that the set of DNA fragments containing the same sequence "S" would give approximately a logarithmic distribution of lengths. In other words, when electrophoresed through a gel where nucleic acid fragments migrate as a logarithmic function of molecular weight, the marker fragments will be approximately evenly spaced and will leave no molecular weight range without a marker. When the pooled, digested DNA is electrophoresed in a gel matrix, a ladder of fragments is generated containing sequence "S", with approximately equal spacing between them.

The probe DNA is complementary to sequence "S", and therefore can be bound specifically to sequence "S" by nucleic acid hybridization. When the probe DNA is labeled (for example, with radioactive phosphorus, biotin, or alkaline phosphatase) it allows visualization of the DNA fragments containing sequence "S".

The present invention preferably utilizes internal labeling sites, thus allowing both ends of the DNA fragment to be altered by restriction endonuclease cleavage. Therefore, a greater variety of DNA fragment sizes can be generated.

The present invention is expected to be useful to research laboratories employing DNA or RNA analysis techniques and it is especially useful to laboratories and law enforcement agencies using DNA analysis to identify individuals.

BRIEF DESCRIPTION OF THE DRAWINGS

FIG. 1 is a schematic, scale drawing of the how the first and second molecular marker kits would migrate on an electrophoretic gel. The positions were calculated by assuming that relative mobilities are a linear function of the logarithm of the length of the fragment in base pairs (bp). The length of each band in bp is indicated to the left of the band.

DETAILED DESCRIPTION OF THE INVENTION

The present invention is a DNA size marker system, preferably a DNA marker ladder, having pooled DNA restriction endonuclease digests. By the term "DNA marker ladder" is meant DNA fragments of varying sizes containing the sequence "S" that when electrophoresed through a gel matrix migrate with approximately equal spacing between them. "Equal spacing" may refer either to the physical location on a gel after electrophoresis (e.g. bands about 0.5 cm. apart) or to the size being marked (e.g. bands differing in size by 1,000 bp). Each restriction digest contains at least one DNA fragment having an "S" sequence complementary to a probe and one or more other DNA fragments not complementary to the probe. The same probe is thus used for all restriction digests. The region of complementarity between the probe and the first DNA fragment of each digest is a double-stranded segment of the first fragment.

The number of restriction digests pooled is at least 5, preferably at least 10, more preferably at least 15, yet more preferably at least 20, and most preferably at least 25. In the present invention, the largest target fragment is at least 10-fold, preferably 14-fold, and most preferably 17-fold, longer than the smallest target fragment.

In some embodiments, target fragments most similar in size differ in length by defined amounts. As defined herein, the "measure", M, of the difference in size is herein calculated by the formula $M = \log_{10}(U) - \log_{10}(L)$, where U and L are the respective lengths in bp of the upper and lower of the two adjacent bands being compared. This equation is equivalent to $10^M = U/L$. As a means of illustration, Table 1 shows the relationship between M, U, and L, (U and L are in bp) with the latter being held constant at 1,000 bp. Note that if U and L are both changed by the same factor or multiple, M remains constant. For example, bands of 1,059 bp and 1,000 bp and bands of 530 bp and 500 bp both differ in size by measures of 0.025.

Preferably, target fragment pairs most similar in size differ in size by no more than a measure of about 0.1 (e.g. bands of 1,259 bp and 1,000 bp), and, most preferably, by no more than a measure of about 0.075 (e.g. bands of 1,188 bp and 1,000 bp). In other words, bands that after gel electrophoresis and Southern blotting would be adjacent to each other differ in size by no more than a measure of about 0.1. As exemplified herein, the target fragment pairs most similar in size differ in size by at least a measure of about 0.025 (e.g. bands of 1,059 bp and 1,000 bp).

Preferably, the target fragments all anneal to a single probe sequence or its complement. More than one molecular species may be in the probe, provided that each digest contains at least one fragment that can anneal to a probe molecule and at least one fragment that cannot anneal to a probe molecule. Although not meant to be limiting, as exemplified herein, the target fragments are derived from bacteriophage λ. As also exemplified herein, the target fragments may be detected with a probe having sequence present in or a sequence complementary to a sequence present in nucleotides 33,783 to 34,212 of bacteriophage λ.

The present invention may further be included in a kit having, in addition to the target fragments, a probe nucleic acid complementary to target DNA fragments. As exemplified herein, the sequence of the probe is present in or is complementary to a sequence present in nucleotides 33,783 to 34,212 of bacteriophage λ.

The kit may further include an enzyme capable of radioactively labeling the probe, e.g. polynucleotide kinase or the Klenow fragment of *E. coli* DNA polymerase I.

Preferably, the target DNA is constructed from a single bacteriophage or plasmid. The target DNA preferably consists of at least 10 restriction endonuclease digests of that target DNA. Each restriction digest of the target DNA creates one fragment complementary to the probe DNA, and the lengths of these fragments may be distributed in a logarithmic array.

Preferably, the probe DNA is supplied as a pair of synthetic oligonucleotides. Each of the probe oligonucleotides is preferably at least 20 nucleotides in length and are complementary to each other for 15 to 30 base pairs at their 3'-ends. These oligonucleotides can then be labeled by incorporation of labeled nucleotides in a chain extension reaction, with each oligonucleotide serving as a primer and using the other as a template in the chain extension reaction. As an illustration, in the following arrangement the upper and lower case letters are complements of each other:

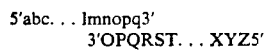

After chain extension with a labeled nucleotide, here indicated by underlining, the oligonucleotides will have the following structure:

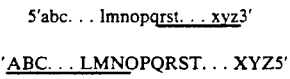

This structure can then be separated to form two probes labeled at their 3'-ends: 5'abc . . . lmnopqrst . . . xyz3' and 5'ZYX . . . TSRQPONML . . . CBA3'.

The probe may be labeled with a radioisotope (e.g. $^3H$, $^{32}P$, $^{35}S$, or $^{125}I$), a ligand (e.g. biotin), a hapten (e.g. dinitrophenol, fluorescein), or an enzyme (e.g. alkaline phosphatase, β-galactosidase, horseradish peroxidase, microperoxidase), or any other suitable labeling method known to or discovered by the art. The choice of labeling method will generally depend on the chosen method for detecting the experimental sample for which the marker kit is serving as a molecular weight standard.

A DNA marker kit of the present invention also include a means for making a probe, instead of just a means for added labeled nucleotides, e.g. with DNA polymerase, or another labeled entity, e.g. $^{32}PO_4$ and kinase. This means may be a means for making an RNA probe. The means for making a probe may include being probe sequences under control of a promoter (i.e. a means-DNA). The kit could also include an RNA polymerase capable of initiating transcription from the promoter and transcribing probe sequences of the means-DNA. Examples of such means-DNAs and RNA polymerases are well known in the art. For instance, DNA sequences downstream from SP6 promoters are commonly transcribed in vitro by SP6 RNA polymerase and sequences downstream from T7 promoters are commonly transcribed in vitro by T7 RNA polymerase.

In an actual gel electrophoresis, the bands may not be spaced exactly as shown in FIG. 1 due to well known phenomena concerning mobility of very large and very small fragments, sample loading effects, and inhomogeneities in the gel. With the use of the present invention, these effects can be detected more readily. Indeed, due to the way that DNA fragments run in 1.0% agarose gels, the largest (e.g. above 10 kbp) target fragments of the exemplified kits will appear more evenly spaced than as illustrated in FIG. 1.

The DNA marker fragments should be hybridized with the probe, with the fragments which bind probe molecules being the fragments detected. When the total DNA of these ladder kits is inspected by non-specific, sequence-independent staining, e.g. with ethidium bromide, the ladder DNA may appear as a "smear" due to the multitude of fragments.

Although specific restriction endonucleases are recited in the Examples and the Claims, it will be recognized that isoschizomers, i.e. enzymes that have the same recognition sequence but cut in a different fashion, can be substituted and the same result will be achieved.

EXAMPLES

Example 1: Common Materials and Methods

*E. coli* bacteriophage λ (lambda) DNA (cIind 1, ts857, Sam 7) was the source of all target DNAs.

The probe DNA for either of the ladders exemplified herein may consist of any DNA from between nucleotides 33,783 and 34,212 of that λ DNA. Oligonucleotides were synthesized using standard phosphoramidite chemistry well known to the art.

To make a restriction digest, λ DNA was digested with one or two restriction endonucleases. The enzymes used for individual digests are indicated in Tables 2 and 3. Digestions were performed under standard conditions, generally according to the instructions of the enzyme's manufacturer. Restriction digests were pooled after digestion.

Example 2: First Marker Kit

In the first ladder, the target DNA consisted of pooled equal amounts of 31 different restriction digests of phage λ DNA. The probe DNA was a 26-base oligonucleotide having a sequence of

5'GCGACATTGCTCCGTGTATTCACTCG3' which is complementary to nucleotides 34,000 to 34,025 of the standard λ DNA map. This oligonucleotide was labeled at its 5'-end by T4 polynucleotide kinase and [γ-$^{32}$P]-ATP (BRL cat. no. 8060SA, Life Technologies, Inc., Gaithersburg, Md.). Hybridization of $^{32}$P-labeled probe DNA to a Southern blot of the target DNA revealed bands of the expected pattern (FIG. 1). The restriction endonuclease digestions used, the sizes of the fragments generated thereby, the λ sequence coordinates thereof, and the measures of the size differences between adjacent bands are listed in Table 2.

Example 3: Second Marker Kit

This first kit was improved in three ways. The first improvement was to change the probe DNA such that (a) it could easily be labeled with DNA polymerase as well as polynucleotide kinase, and (b) it would remain hybridized to the Southern blot even when washed at high temperature (65° C.) and low salt concentration (0.015M NaCl). This was achieved by utilizing two 70-base, synthetic oligonucleotides that were complementary to opposite strands of λ DNA, and also complementary to one another for 15 bases at their 3'-termini. The two oligonucleotides were as follows:

and measures of the size differences between adjacent bands are listed in Table 3.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

TABLE 1

Examples of Relationships between the Measure of the Difference in Size and Sizes of Fragments.

| M | U | L |
|---|---|---|
| 0.0 | 1,000 | 1,000 |
| 0.025 | 1,059 | 1,000 |
| 0.05 | 1,122 | 1,000 |
| 0.075 | 1,188 | 1,000 |
| 0.1 | 1,259 | 1,000 |
| 0.15 | 1,413 | 1,000 |
| 0.2 | 1,585 | 1,000 |
| 0.3 | 1,995 | 1,000 |
| 0.5 | 3,162 | 1,000 |
| 0.7 | 5,012 | 1,000 |
| 1.0 | 10,000 | 1,000 |

$M = \log_{10}(U) - \log_{10}(L)$ = Measure of the difference in size.
$U$ = Size in bp of the upper band in a comparison.
$L$ = Size in bp of the lower band in a comparison, held constant at 1,000 bp.

TABLE 2

5'AGGCCACTATCAGGCAGCTTTGTTGTTCTGTTTACCAAGTTCTCTGGCAATCATT<u>GCCGTCGTTCGTATT</u>3'

5'AGCCTGAAGAAATGTTTCCTGTAATGGAAGATGGGAAATATGTCGATAAATGGG<u>AATACGAACGACGGC</u>3'

The underlined segments are complementary to each other. The first oligonucleotide is encoded by sequences from coordinates 34,078 (5'-end) to 34,147 (3'-end) and the second oligonucleotide is encoded by sequences from 34,133 (3'-end) to 34,202 (5'-end) on the standard λ map. These oligonucleotides were mixed together with each other and the Klenow fragment of E. coli DNA polymerase I and four deoxynucleotide triphosphates, one of which was α-$^{32}$P-labelled. The polymerase extended each oligonucleotide using the other as a template and produced two α-$^{32}$P-labelled, complementary oligonucleotides. This new probe hybridizes to the same target fragments as the previous probe. A mixture of the new 70-mers was labeled with the large fragment of E. coli DNA polymerase I and hybridized to a Southern blot of the target DNA.

The second improvement was to change the target DNA to give a more linear spacing on the Southern blot.

The third improvement was to increase the amounts, i.e. relative copy number or the dosage, of the target DNA for the largest and smallest bands. Large DNA fragments blot inefficiently. As is well known in the art, small fragments are retained on membranes poorly during hybridization. Therefore, the signal from large DNA fragments and small DNA fragments tends to be less than the signal from bands in the middle range. This improvement compensated for that effect.

Hybridization of $^{32}$P-labeled probe DNA to a Southern blot of the target DNA revealed bands of the expected pattern (FIG. 1). The restriction endonuclease digestions and dosage used, the sizes of the fragments generated thereby, the λ sequence coordinates thereof, DNA Analysis Marker Ladder Target DNA Fragments. First Kit

| Enzyme(s) | Size | Diff. | Lambda Coordinates Left | Right |
|---|---|---|---|---|
| Xba I* | 23,994 | 0.204 | 24,508 | 48,502 |
| Xho I | 15,004 | 0.127 | 33,498 | 48,502 |
| Xba I/Bgl II* | 11,203 | 0.075 | 24,508 | 35,711 |
| Hind III | 9,416 | 0.056 | 27,479 | 36,895 |
| Sma I | 8,271 | 0.047 | 31,619 | 39,890 |
| EcoR I | 7,421 | 0.061 | 31,747 | 39,168 |
| Ava II | 6,442 | 0.041 | 32,562 | 39,004 |
| Hae II | 5,861 | 0.034 | 28,859 | 34,720 |
| EcoR V/Ava II | 5,415 | 0.060 | 33,589 | 39,004 |
| Ava I | 4,716 | 0.067 | 33,498 | 38,214 |
| Bgl I/BstE II* | 4,045 | 0.026 | 32,329 | 36,374 |
| Ava II/BstE II | 3,812 | 0.025 | 32,562 | 36,374 |
| Dra I* | 3,599 | 0.065 | 32,705 | 36,304 |
| Sma I/Hae II | 3,101 | 0.033 | 31,619 | 34,720 |
| Xho I/BstE II | 2,876 | 0.036 | 33,498 | 36,374 |
| Nci I | 2,650 | 0.037 | 33,158 | 35,808 |
| Nde I | 2,433 | 0.026 | 33,680 | 36,113 |
| Msp I* | 2,293 | 0.056 | 33,157 | 35,450 |
| Hinc II | 2,015 | 0.035 | 33,246 | 35,261 |
| EcoR V/Msp I | 1,861 | 0.023 | 33,589 | 35,450 |
| Xho I/Hinc II* | 1,763 | 0.051 | 33,498 | 35,261 |
| Rsa I | 1,568 | 0.040 | 32,868 | 34,436 |
| Ssp I | 1,431 | 0.028 | 33,572 | 35,003 |
| Msp I/BamH I* | 1,342 | 0.057 | 33,157 | 34,499 |
| Sau3A I | 1,176 | 0.024 | 33,323 | 34,499 |
| Cla I* | 1,112 | 0.087 | 33,585 | 34,697 |
| EcoR V/BamH I | 910 | 0.033 | 33,589 | 34,499 |
| Hinf I* | 844 | 0.064 | 33,783 | 34,627 |
| EcoR V/Cvn I* | 730 | 0.048 | 33,589 | 34,319 |
| Hinf I/Rsa I | 653 | 0.094 | 33,783 | 34,436 |
| Nsi I | 526 | — | 33,686 | 34,212 |

Diff. = The difference. M. in size between the band and the band immediately below, calculated by the formula, $M = \log_{10}(U) - \log_{10}(L)$, where U and L are the lengths in bp of the upper and lower, respectively, of the two bands being compared.
*indicates enzyme combinations used in the first ladder but not used in the second ladder.

TABLE 3

DNA Analysis Marker Ladder Target DNA Fragments, Second Kit

| Enzyme(s) | Size | Diff. | Lambda Coordinates Left | Lambda Coordinates Right | Dose |
|---|---|---|---|---|---|
| Sst I* | 22,621 | 0.178 | 25,881 | 48,502 | 3 |
| Xho I | 15,004 | 0.100 | 33,498 | 48,502 | 3 |
| Nco I/Bgl I* | 11,919 | 0.102 | 32,329 | 44,248 | 3 |
| Hind III | 9,416 | 0.056 | 27,479 | 36,895 | 3 |
| Sma I | 8,271 | 0.047 | 31,619 | 39,890 | 3 |
| EcoR I | 7,421 | 0.061 | 31,747 | 39,168 | 3 |
| Ava II | 6,442 | 0.041 | 32,562 | 39,004 | 3 |
| Hae II | 5,861 | 0.034 | 28,859 | 34,720 | 1 |
| EcoR V/Ava II | 5,415 | 0.060 | 33,589 | 39,004 | 1 |
| Ava I | 4,716 | 0.037 | 33,498 | 38,214 | 1 |
| Ava II/Hind III* | 4,333 | 0.056 | 32,562 | 36,895 | 1 |
| Ava II/BstE II | 3,812 | 0.050 | 32,562 | 36,374 | 1 |
| Xho I/Hind III* | 3,397 | 0.040 | 33,498 | 36,895 | 1 |
| Sma I/Hae II | 3,101 | 0.033 | 31,619 | 34,720 | 1 |
| Xho I/BstE II | 2,876 | 0.036 | 33,498 | 36,374 | 1 |
| Nci I | 2,650 | 0.037 | 33,158 | 35,808 | 1 |
| Nde I | 2,433 | 0.041 | 33,680 | 36,113 | 1 |
| Xho I/Bgl II* | 2,213 | 0.041 | 33,498 | 35,711 | 1 |
| Hinc II | 2,015 | 0.035 | 33,246 | 35,261 | 1 |
| EcoR V/Msp I | 1,861 | 0.047 | 33,589 | 35,450 | 1 |
| EcoR V/Hinc II* | 1,672 | 0.028 | 33,589 | 35,261 | 1 |
| Rsa I | 1,568 | 0.040 | 32,868 | 34,436 | 1 |
| Ssp I | 1,431 | 0.046 | 33,572 | 35,003 | 1 |
| Tha I/Rsa I* | 1,287 | 0.039 | 33,149 | 34,436 | 1 |
| Sau3A I | 1,176 | 0.073 | 33,323 | 34,499 | 1 |
| Cfo I* | 993 | 0.038 | 33,726 | 34,719 | 1 |
| EcoR V/BamH I | 910 | 0.065 | 33,589 | 34,499 | 1 |
| Dde I* | 784 | 0.079 | 33,535 | 34,319 | 3 |
| Hinf I/Rsa I | 653 | 0.094 | 33,783 | 34,436 | 3 |
| Nsi I | 526 | — | 33,686 | 34,212 | 3 |

Diff. = The difference, M, in size between the band and the band immediately below, caculated by the formula $M = \log_{10}(U) \cdot \log_{10}(L)$, where U and L are the lengths in bp of the upper and lower, respectively, of the two bands being compared.
*indicates enzyme combinations used in the second ladder but not used in the first ladder.
Dose refers to the relative amounts of each restriction digest.

What is claimed is:

1. A DNA marker system comprising at least 5 DNA restriction endonuclease digests pooled together and a single nucleic acid probe, wherein
   (1) a DNA restriction endonuclease digest is a collection of DNA fragments resulting from digestion of a DNA by one or more restriction endonucleases,
   (2) each restriction digest is obtained from the same DNA molecule;
   (3) each restriction digest contains a first DNA fragment complementary to said probe,
   (4) each restriction digest contains at least one second DNA fragment not complementary to said probe,
   (5) the region of complementarity between said probe and the first DNA fragment of each digest is a double stranded segment of the first fragment, and
   (6) wherein when said DNA restriction digests are separated by electrophoresis and annealed to said probe, a detectably labeled DNA marker ladder is obtained.

2. A system as in claim 1, comprising at least 10 DNA restriction endonuclease digests pooled together.

3. A system as in claim 2, comprising at least 15 DNA restriction endonuclease digests pooled together.

4. A system as in claim 3, comprising at least 20 DNA restriction endonuclease digests pooled together.

5. A system as in claim 4, comprising at least 25 DNA restriction endonuclease digests pooled together.

6. A system as in claim 1, wherein adjacent target fragment pairs differ in size by no more than a measure of about 0.1.

7. A system as in claim 6, wherein adjacent target fragment pairs differ in size by no more than a measure of about 0.075.

8. A system as in claim 1, wherein adjacent target fragment pairs differ in size by at least a measure of about 0.025.

9. A system as in claim 6, wherein adjacent target fragment pairs differ in size by at least a measure of about 0.025 and by no more than a measure of about 0.075.

10. A system as in claim 1, wherein the largest target fragment is at least 10-fold longer than the smallest target fragment.

11. A system as in claim 10, wherein the largest target fragment is at least 14-fold longer than the smallest target fragment.

12. A system as in claim 11, wherein the largest target fragment is at least 17-fold longer than the smallest target fragment.

13. A system as in claim 1, wherein the target fragments are derived from bacteriophage λ.

14. A system as in claim 13, wherein the target fragments may be detected with a probe having sequence present in or a sequence complementary to a sequence present in nucleotides 33,783 to 34,212 of bacteriophage λ.

15. A system as in claim 14, wherein the target fragments include at least 10 fragments are chosen from a group of DNA fragments having sizes and ends of 11,203 bp Xba I/Bgl II, 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 4,045 bp Bgl I/BstE II, 3,812 bp Ava II/BstE II, 3,599 bp Dra I, 3,397 bp Xho I/Hind III, 3,101 bp Sma I/Hae II, 2,876 bp Xho I/BstE II, 2,650 bp Nci I, 2,433 bp Nde I, 2,293 bp Msp I, 2,213 bp Xho I/Bgl II, 2,015 bp Hinc II, 1,861 bp EcoR V/Msp I, 1,763 bp Xho I/Hinc II, 1,672 bp EcoR V/Hinc II, 1,568 bp Rsa I, 1,431 bp Ssp I, 1,342 bp Msp I/BamH I, 1,287 bp Tha I/Rsa I, 1,176 bp Sau3A I, 1,112 bp Cla I, 993 bp Cfo I, 910 bp EcoR V/BamH I, 844 bp Hinf I, 784 bp Dde I, 730 bp EcoR V/Cvn I, and 653 bp Hinf I/Rsa I.

16. A system as in claim 15, wherein the target fragments include at least 15 fragments and are chosen from a group of DNA fragments having sizes and ends of 11,203 bp Xba I/Bgl II, 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 4,045 bp Bgl I/BstE II, 3,812 bp Ava II/BstE II, 3,599 bp Dra I, 3,397 bp Xho I/Hind III, 3,101 bp Sma I/Hae II, 2,876 bp Xho I/BstE II, 2,650 bp Nci I, 2,433 bp Nde I, 2,293 bp Msp I, 2,213 bp Xho I/Bgl II, 2,015 bp Hinc II, 1,861 bp EcoR V/Msp I, 1,763 bp Xho I/Hinc II, 1,672 bp EcoR V/Hinc II, 1,568 bp Rsa I, 1,431 bp Ssp I, 1,342 bp Msp I/BamH I, 1,287 bp Tha I/Rsa I, 1,176 bp Sau3A I, 1,112 bp Cla I, 993 bp Cfo I, 910 bp EcoR V/BamH I, 844 bp Hinf I, 784 bp Dde I, 730 bp EcoR V/Cvn I, and 653 bp Hinf I/Rsa I.

17. A system as in claim 16, wherein the target fragments comprise at least 20 fragments and are chosen from a group of DNA fragments having sizes and ends of 11,203 bp Xba I/Bgl II, 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 4,045 bp Bgl I/BstE II, 3,812 bp Ava II/BstE II, 3,599 bp Dra I, 3,397 bp Xho II/Hind III, 3,101 bp Sma II/Hae II, 2,876 bp Xho II/BstE II, 2,650 bp Nci I, 2,433 bp Nde I, 2,293 bp Msp I, 2,213 bp Xho I/Bgl II, 2,015 bp Hinc II, 1,861 bp EcoR V/Msp I, 1,763 bp Xho I/Hinc II, 1,672 bp EcoR V/Hinc II, 1,568 bp Rsa I, 1,431 bp Ssp I, 1,342 bp Msp I/BamH I, 1,287 bp Tha I/Rsa I, 1,176 bp Sau3A I, 1,112 bp Cla I, 993 bp Cfo I, 910 bp EcoR V/BamH I, 844 bp Hinf I, 784 bp Dde I, 730 bp EcoR V/Cvn I, and 653 bp Hinf I/Rsa I.

18. A system as in claim 17, wherein the target fragments comprise at least 25 fragments and are chosen from a group of DNA fragments having sizes and ends of 11,203 bp Xba I/Bgl II, 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 4,045 bp Bgl I/BstE II, 3,812 bp Ava II/BstE II, 3,599 bp Dra I, 3,397 bp Xho I/Hind III, 3,101 bp Sma I/Hae II, 2,876 bp Xho I/BstE II, 2,650 bp Nci I, 2,433 bp Nde I, 2,293 bp Msp I, 2,213 bp Xho I/Bgl II, 2,015 bp Hinc II, 1,861 bp EcoR V/Msp I, 1,763 bp Xho I/Hinc II, 1,672 bp EcoR V/Hinc II, 1,568 bp Rsa I, 1,431 bp Ssp I, 1,342 bp Msp I/BamH I, 1,287 bp Tha I/Rsa I, 1,176 bp Sau3A I, 1,112 bp Cla I, 993 bp Cfo I, 910 bp EcoR V/BamH I, 844 bp Hinf I, 784 bp Dde I, 730 bp EcoR V/Cvn I, and 653 bp Hinf I/Rsa I.

19. A system as in claim 17, wherein the target fragments comprise at least 25 fragments and are chosen from a group of DNA fragments having sizes and ends of 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 3,812 bp Ava II/BstE II, 3,397 bp Xho I/Hind III, 3,101 bp Sma I/Hae II, 2,876 bp Xho I/BstE II, 2,650 bp Nci I, 2,433 bp Nde I, 2,213 bp Xho I/Bgl II, 2,015 bp Hinc II, 1,861 bp EcoR V/Msp I, 1,672 bp EcoR V/Hinc II, 1,568 bp Rsa I, 1,431 bp Ssp I, 1,287 bp Tha I/Rsa I, 1,176 bp Sau3A I, 993 bp Cfo I, 910 bp EcoR V/BamH I, 784 bp Dde I, and 653 bp Hinf I/Rsa I.

20. A system as in claim 19, wherein the target fragments have sizes and ends of 22,621 bp Sst I, 15,004 bp Xho I, 11,919 bp Nco I/Bgl I, 9,416 bp Hind III, 8,271 bp Sma I, 7,421 bp EcoR I, 6,442 bp Ava II, 5,861 bp Hae II, 5,415 bp EcoR V/Ava II, 4,716 bp Ava I, 4,333 bp Ava II/Hind III, 3,812 bp Ava II/BstE II, 3,397 bp Xho I/Hind III, 3,101 bp Sma I/Hae II, 2,876 bp Xho I/BstE II, 2,650 bp Nci I, 2,433 bp Nde I, 2,213 bp Xho I/Bgl II, 2,015 bp Hinc II, 1,861 bp EcoR V/Msp I, 1,672 bp EcoR V/Hinc II, 1,568 bp Rsa I, 1,431 bp Ssp I, 1,287 bp Tha I/Rsa I, 1,176 bp Sau3A I, 993 bp Cfo I, 910 bp EcoR V/BamH I, 784 bp Dde I, 653 bp Hinf I/Rsa I, and 526 bp Nsi I.

21. A system as in claim 1, wherein relative quantities of each fragment is such that in a Southern blot hybridization observed band intensities are uniform within a factor of 2.

22. A DNA marker kit comprising
(a) a DNA marker system comprising at least 5 DNA restriction endonuclease digests pooled together, wherein
(1) a DNA restriction endonuclease digest is a collection of DNA fragments resulting from digestion of a DNA by one or more restriction endonucleases,
(2) each restriction digest is obtained from the same DNA molecule;
(3) each restriction digest contains a first DNA fragment complementary to a probe,
(4) each restriction digest contains at least one second DNA fragment not complementary to said probe,
(5) the region of complementarity between said probe and the first DNA fragment of each digest is a double stranded segment of the first fragment, and
(b) a first probe nucleic acid which is complementary to said first target DNA fragments;
wherein when said DNA restriction digests are separated by electrophoresis and annealed to said probe, a detectably labeled DNA marker ladder is obtained.

23. A kit as in claim 22, further comprising a second probe nucleic acid complementary to target DNA fragments, wherein the first probe and the second probe are DNA, are complementary to each other at their 3'-ends, and are not complementary to each other at their 5'-ends.

24. A kit as in claim 22, wherein the sequence of the first probe is present in or is complementary to a sequence present in nucleotides 33,783 to 34,212 of bacteriophage λ.

25. A kit as in claim 22, further comprising an enzyme capable of labeling the probe.

26. A kit as in claim 25, further comprising an enzyme capable of radioactively labeling the probe.

27. A kit as in claim 25, wherein the enzyme is a DNA polymerase.

28. A kit as in claim 27, wherein the enzyme is the Klenow fragment of *E. coli* DNA polymerase I.

29. A kit as in claim 25, wherein the enzyme is polynucleotide kinase.

30. A DNA marker kit comprising the DNA marker system of claim 1 and a means for making a probe.

31. A kit as in claim 30, wherein the means for making a probe is a means for making an RNA probe.

32. A kit as in claim 31, wherein the means for making a probe comprises
(a) a means-DNA, wherein the means-DNA comprises probe sequences under control of a promoter, and
(b) an RNA polymerase capable of initiating transcription from the promoter and transcribing probe sequences of the means-DNA.

* * * * *